United States Patent [19]

Bremer

[11] Patent Number: 4,691,698

[45] Date of Patent: Sep. 8, 1987

[54] TIBIAL TORSION SPLINT WITH MULTIPLE DEGREES OF FREEDOM OF ADJUSTMENT

[76] Inventor: Ross L. Bremer, c/o 433 Margaret St., Jacksonville, Fla. 32204

[21] Appl. No.: 852,819

[22] Filed: Apr. 16, 1986

[51] Int. Cl.$^4$ ............................................. A61F 3/00
[52] U.S. Cl. ................ 128/80 R; 128/87 C; 128/88
[58] Field of Search ............ 128/88, 87 C, 87 R, 128/80 A, 80 B, 80 C, 80 F, 80 J, 80 R

[56] References Cited

U.S. PATENT DOCUMENTS

| D. 273,897 | 5/1984 | Bremer | 128/80 R X |
|---|---|---|---|
| 532,461 | 1/1895 | Hoppe | 128/88 |
| 1,340,630 | 5/1920 | Maddox | 128/88 |
| 1,639,815 | 8/1927 | Siebrandt | 128/88 |
| 2,630,801 | 3/1953 | Mest et al. | 128/80 A |
| 3,086,522 | 4/1963 | Frohmader | 128/80 J |
| 3,304,937 | 2/1967 | Callender, Jr. | 128/80 R |
| 3,777,747 | 12/1973 | Friedman | 128/80 A |
| 3,958,567 | 5/1976 | Callender, Jr. | 128/80 R |

FOREIGN PATENT DOCUMENTS

| 93293 | 8/1897 | Fed. Rep. of Germany | 128/88 |
|---|---|---|---|
| 415598 | 6/1925 | Fed. Rep. of Germany | 128/88 |
| 878286 | 11/1981 | U.S.S.R. | 128/88 |

OTHER PUBLICATIONS

Bremer Orthopedics brochure, "The Right Angle Splint", 1983.

Primary Examiner—Clifford D. Crowder
Attorney, Agent, or Firm—Nixon & Vanderhye

[57] ABSTRACT

A tibial torsion splint allows for the adjustment of a foot plate and a leg support with respect to a frame so as to accommodate a user who is knock-kneed, or has a related condition; and to control pronation and supination in a simple yet effective manner, while still providing conventional external and internal adjustment of the foot plate, and adjustment of the spacing between the leg support and the foot plate. A circular cross-section rod and a pair of U-clamps which are connected to the foot plate and the leg support, respectively, by threaded fasteners, comprise a strong frame while also accommodating the various adjustments that are necessary. Straps are associated with portions of a right angle member which defines the leg support, the straps having a rigid backing which is adjustably positioned over the length of the rigid angle member, a wide padded portion, and a narrow fastening portion preferably having hook and pile fasteners.

20 Claims, 4 Drawing Figures

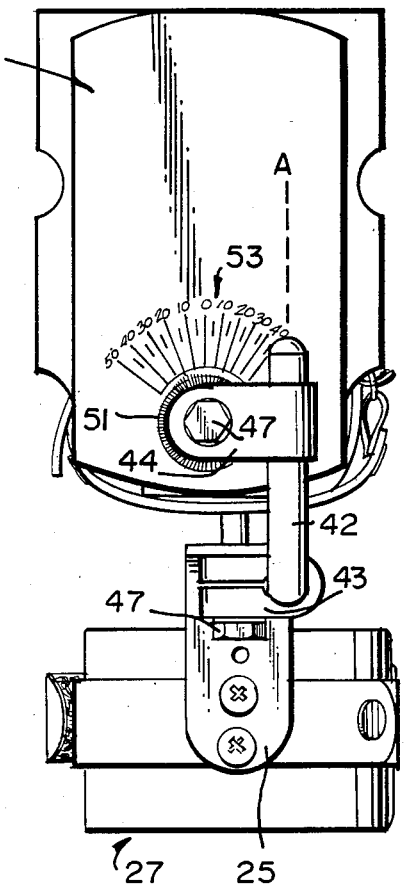
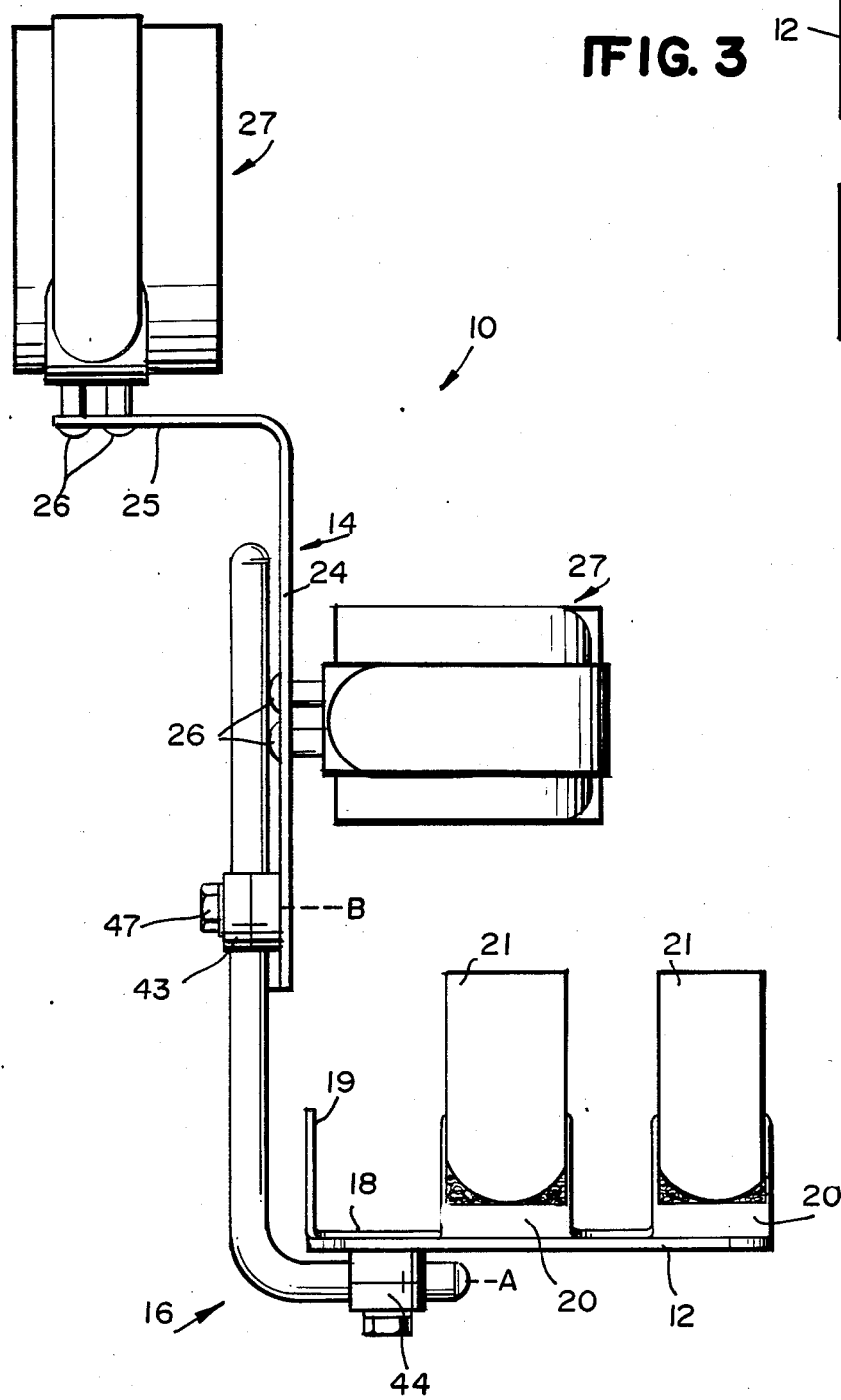
FIG. 3
FIG. 1

TIBIAL TORSION SPLINT WITH MULTIPLE DEGREES OF FREEDOM OF ADJUSTMENT

BACKGROUND AND SUMMARY OF THE INVENTION

There have been a wide variety of orthopedic braces which have been proposed, and commercially utilized, to correct undesired conditions of the leg and/or foot of a user, particularly for infants and children. It is desirable in providing such a structure to have a strong construction yet still allow for a wide variety of adjustments of components thereof to accommodate and/or correct different conditions that the user may have, and to accommodate different lengths of the user's tibia or other parts of the user's leg. It is also desirable to accomplish these results with a device that is relatively light in weight and easily worn by the user, and easily shipped.

Heretofore, all of the above desirable characteristics and requirements of orthopedic appliances have not been provided in a single structure. However according to the present invention a tibial torsion splint is provided which has all the necessary desirable features.

The tibial torsion splint according to the present invention has a circular cross-section rod having first and second generally perpendicular portions, which comprises the main structure of the frame. The circular rod structure provides great strength and flexibility of use. The frame also comprises a pair of U-shaped clamps, with fasteners extending through portions of the clamps to engage the foot plate and leg support components, respectively. Release of the fastener associated with the clamp engaging the foot plate allows both external and internal adjustment of the foot plate, and in addition provides a very simple structure for controlling pronation and supination. The clamp and rod portion associated with the leg support component allows for adjustment of the position of the leg support component with respect to the frame to accommodate users having knock-knees or like conditions, and additionally provides a simple structure for adjustment of the spacing between the plate and the leg support to accommodate users having tibias of different lengths.

Also according to the present invention, the components are made of aluminum and therefore very light in weight, and have a streamlined design. The leg supporting component comprises a rigid right angle member with a strap assembly associated with each portion of the rigid right angle member. Each strap assembly includes a rigid arcuate portion which is actually connected to the right angle member, as by fasteners, and can be adjustably positioned along the length of the right angle member. Connected to the rigid arcuate member is a relatively wide strap which has a cushioning character (which may be provided by constructing the wide strap, at least in part, of a foam), and a narrow strap with fasteners holds the wide strap in the appropriate position on the user's leg. The narrow strap preferably comprises a single band of flexible material which has hook fasteners connected to one part of the band, and pile fasteners connected to the other, so that it can be passed through a D-ring and back on itself to fasten the strap in proper position.

It is the primary object of the present invention to provide a strong, streamlined, and versatile orthopedic appliance. This and other objects of the invention will become clear from an inspection of the detailed description of the invention, and from the appended claims.

BRIEF DESCRIPTION OF THE DRAWINGS

FIG. 1 is a side view of an exemplary tibial torsion splint according to the present invention;

FIG. 3 is a bottom view of the splint of FIG. 1; and

DETAILED DESCRIPTION OF THE DRAWINGS

Figure 2:
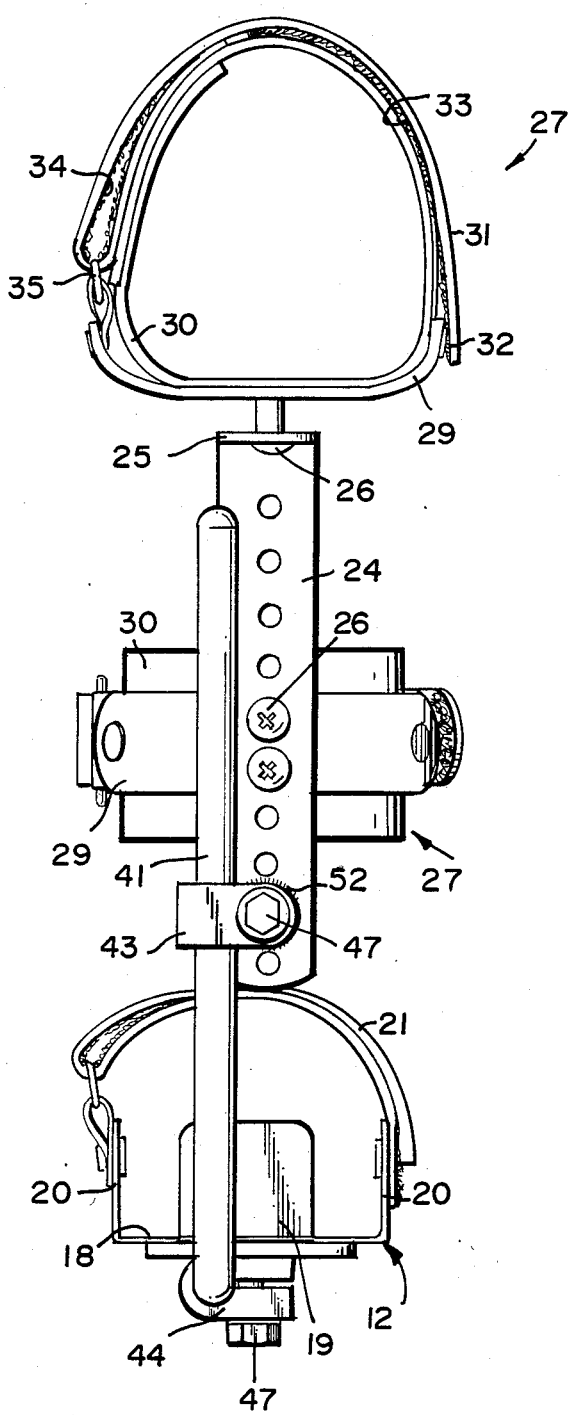
FIG. 2 is a rear view of the splint of FIG. 1.

Major components of the tibial torsion splint 10 according to the present invention include the foot plate 12, leg support means 14, and frame means 16.

The foot plate 12 and the leg support means 14 are known per se. The foot plate 12 includes a heel supporting portion 18, a heel backing portion 19, side components 20, and straps 21 for connecting a user's shoed foot to the plate.

The leg support means 14 comprises a rigid (aluminum) right angle member having a first portion 24 and a second portion 25, each of which preferably has a plurality of holes along the length thereof to accommodate threaded fasteners 26 associated with strap assemblies 27. Each strap assembly 27 includes an arcuate rigid backing component 29, which is attached to a flexible relatively wide padded strap 30, with a relatively narrow strap 31 having fasteners associated therewith for holding the strap 30 in engagement with a user's leg. The narrow strap 31 is affixed at one end 32 thereof, and has pile fasteners 33 attached to one portion thereof and hook fasteners 34 attached to another portion thereof. The strap 31 passes through a D-ring 35 and folds back over itself so that the hook and pile portions 34, 33 engage each other and hold the strap assembly 27 in place on a user.

According to the present invention a novel and strong frame 16 is provided. The major portions of the frame include the circular cross-section aluminum rod 40 having a first portion 41 thereof, and a second portion 42. The portions 41, 42 are approximately at a right angle to each other (preferably they make an angle of about 94° with respect to each other). Associated with the aluminum rod 40 are first and second clamps 43, 44 respectively. Each clamp is generally U-shaped, having legs 45 which are open at one end thereof, and which receive the rod 40 at a second end 46 thereof. A threaded fastener, such as bolt 47, passes through the U-shaped clamp legs 45 adjacent the first end thereof, the threaded fastener 47 engaging an interiorly threaded hole associated with the foot plate 12 or the right angle member portion 24.

Figure 4:
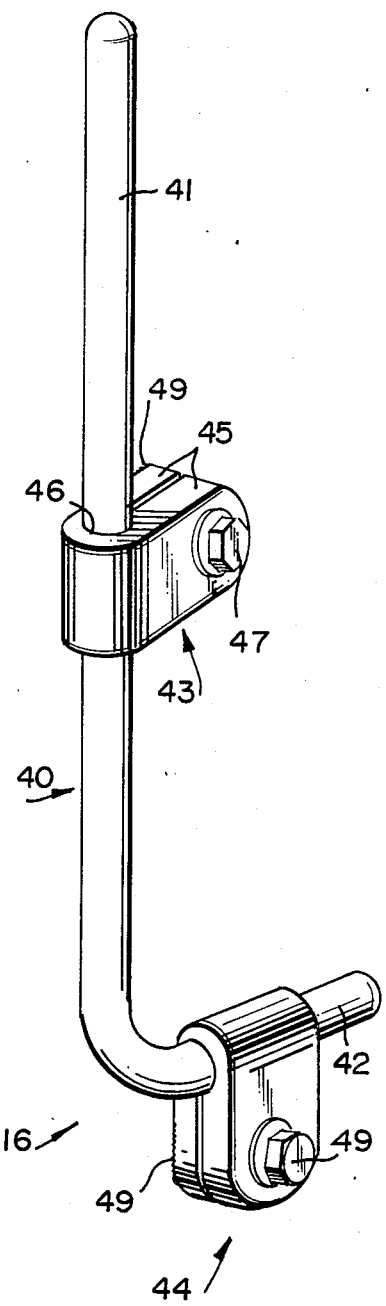
FIG. 4 is a detail perspective view of the circular cross-section rod and clamp components of the frame of the device of FIGS. 1 through 3.

The face of each clamp 43, 44 engaging foot plate 12 (or the portion 24) is serrated, as indicated schematically at 49 in FIG. 4, the serrations thereon engaging corresponding serrations 51 on the bottom of foot plate 12, or serrations 52 on the back face of rigid angle member portion 24 (see FIGS. 3 and 2, respectively). The serrations 49, 51, 52 allow positive positioning of the components at various angular positions with respect to each other. Preferably indicia 53 (see FIG. 3) are provided in a known manner on the bottom of the foot plate 12 to allow precise external and internal adjustment of the foot plate 12 with respect to the frame 16 (and clamp 44 thereof).

According to the present invention, pronation and supination can be controlled in a very simple yet effective manner utilizing the improved frame 16. Since the rod portion 42 is circular in cross-section and defines an axis A (see FIGS. 1 and 3) that is parallel to (and below) the foot plate 12, when the fastener 47 is released and the clamp 44 no longer tightly engages it, the clamp 44 (and the foot plate to which it is still attached by the threaded fastener 47) may be rotated about the axis A, controlling pronation and supination.

According to the present invention, easy adjustability of the leg support means 14 to accommodate users who have knock-knees, or related conditions, is also provided. This is accomplished merely by loosening the fastener 47 to allow rotation of the clamp 43 with respect to the right angle member portion 24, the fastener 47 associated with the clamp 43 defining an axis B (see FIG. 3) that is above, and generally parallel to, the plate 12. Also, the clamp 43, fastener 47, and rod portion 41 allow for ready adjustability of the position of the leg support 14 with respect to the plate 12 to accommodate users having tibias of different length, this being accomplished by loosening the fastener 47 so that the clamp 43 does not tightly engage the rod portion 41, and then sliding the clamp 43 upwardly or downwardly along the length of the rod portion 41. The fastener 47 associated with the clamp 43 engages an interiorly threaded opening (not shown) in the right angle member 24.

It will thus be seen that according to the present invention a tibial torsion splint has been provided that is strong, is lightweight (all the metal components thereof being made of aluminum or the like, and the components being simple), is streamlined in configuration, and is very versatile accommodating users having a wide variety of size of their leg and foot portions, and accommodating and/or correcting a wide variety of user conditions. The invention provides for control of pronation and supination of the foot, for external or internal rotation of the foot, for adjustments of the spacing between the leg support and the foot plate, and the straps along the leg support, to accommodate users having tibias of different length, and the like, and accommodates users who have knock-knees or like conditions. While the invention has been herein shown and described in what is presently conceived to be the most practical and preferred embodiment thereof it will be apparent to those of ordinary skill in the art that many modifications may be made thereof within the scope of the invention, which scope is to be accorded the broadest interpretation of the appended claims so as to encompass all equivalent structures and devices.

What is claimed is:

1. A tibial torsion splint comprising:
a foot plate adapted to receive the foot of a user;
leg support means for supporting a user's leg adjacent both the upper and lower parts of the user's knee;
frame means interconnecting said plate and said leg support means;
first means for connecting said foot plate to said frame means for rotation of said foot plate about axes respectively generally perpendicular and parallel to said plate;
second means for adjusting the position of said leg support means with respect to said foot plate to accommodate users having tibias of different length; and
third means for adjusting the rotational position of said leg support means with respect to said frame means about an axis generally parallel to the plane of said foot plate and spaced from the first mentioned axis generally parallel to said plate, to accommodate users with knock-knees, or related conditions.

2. A device as recited in claim 1 wherein said leg support means comprises a rigid angle member having a first portion operatively connected to said frame means, and having a second portion remote from said frame means; each of said first and second portions of said right angle member having strap means associated therewith for attaching said first and second portions to the leg of a user.

3. A device as recited in claim 2 wherein said third means comprises a threaded fastener passing through an operative frame component and engaging said angle member first portion at a position thereof remote from said rigid angle member second portion; release of said fastener allowing relative rotation between said frame operative component and said rigid angle member, and tightening of said fastener holding said operative frame component and said rigid angle member in the position to which they have been rotated.

4. A device as recited in claim 3 wherein said operative frame component comprises a generally U-shaped clamp means for receiving a circular cross-section rod, said clamp means and said rod comprising part of said frame means; and wherein said threaded fastener releasably clamps said rod in position with respect to said rigid angle member, and said clamp means and said rod comprise said second means.

5. A device as recited in claim 4 further comprising means for adjusting the position of said strap means along said rigid angle member.

6. A tibial torsion splint comprising:
a foot plate adapted to receive the foot of a user;
leg support means for supporting a user's leg adjacent both the upper and lower parts of the user's knee;
frame means interconnecting said plate and said leg support means;
first means for connecting said foot plate to said frame means for rotation of said foot plate about an axis generally perpendicular to said plate;
second means for adjusting the position of said leg support means with respect to said foot plate to accommodate users having tibias of different length; and
means for adjusting the positioning of said plate with respect to said frame about an axis parallel to said foot plate, the latter means comprising a circular cross-section rod portion defining an axis parallel to said foot plate, and a clamp releasably clampingly receiving said rod portion and when releasing said rod portion rotatable to various different rotational positions with respect to said rod portion, and clampable in different rotatable positions.

7. A device as recited in claim 6 wherein said leg support means comprises a rigid angle member having a first portion operatively connected to said frame means, and having a second portion remote from said frame means; each of said first and second portions of said right angle member having strap means associated therewith for attaching said first and second portions to the leg of a user.

8. A device as recited in claim 7 wherein said frame means comprises an aluminum rod and clamps.

9. A tibial torsion splint comprising:
a foot plate adapted to receive the foot of a user;

leg support means for supporting a user's leg adjacent both the upper and lower parts of the user's knee;

frame means interconnecting said plate and said leg support means;

first means for connecting said foot plate to said frame means for rotation of said foot plate about an axis generally perpendicular to said plate;

second means for adjusting the position of said leg support means with respect to said foot plate to accommodate users having tibias of different length; and wherein said frame means comprises a circular cross-section rod having first and second portions approximately perpendicular to each other, and a first clamp means for connecting said rod first portion to said leg support means, and a second clamp means for connecting said second rod portion to said plate.

10. A device a recited in claim 9 wherein said first clamp means by releasably clamping said rod first portion provides for adjustment of the spacing between said plate and said leg support means to accommodate users having tibias of different length.

11. A device as recited in claim 10 wherein said leg support means comprises a rigid angle member having a first portion operatively connected to said first clamp means, and having a second portion remote from said first clamp means; each of said first and second portions of said right angle member having strap means associated therewith for attaching said first and second portions to the leg of a user.

12. A device as recited in claim 11 wherein said strap means comprises a first relatively wide strap portion having padding associated therewith and directly engaging the user's leg, and a second relatively narrow strap portion exterior of said first strap portion and having releasable fasteners associated therewith.

13. A device as recited in claim 12 further comprising a rigid arcuate member backing a portion, but only a portion, of said wide strap and connecting said first and second strap portions to said right angle member; and wherein said fastener means associated with said second strap portion comprises hook and pile fasteners.

14. A device as recited in claim 9 wherein said second rod portion and said second clamp means comprise means for adjusting the position of said plate with respect to an axis parallel to, and below, said plate, said second rod portion defining said axis parallel to said plate.

15. A device as recited in claim 14 wherein said first rod portion and said first clamp means comprise means for adjusting the rotational position of said leg support means with respect to said frame about an axis generally parallel to, and above, said plate to accommodate users having knock-knees or related conditions.

16. A device as recited in claim 15 wherein said clamp means each comprise a U-shaped clamp having leg portions that are open at one end, and receive said circular cross-section rod portions at an opposite end; and wherein release of said clamp means is provided by a threaded fastener which passes through said legs adjacent said open end thereof, said threaded fastener also threadedly engaging either said foot plate or said leg support means.

17. A device as recited in claim 16 wherein said leg support means comprises a rigid angle member having a first portion operatively connected to said first clamp means, and having a second portion remote from said first clamp means; each of said first and second portions of said right angle member having strap means associated therewith for attaching said first and second portions to the leg of a user.

18. A device as recited in claim 9 wherein said first rod portion and said first clamp means comprise means for adjusting the rotational position of said leg support means with respect to said frame about an axis generally parallel to, and above, said plate to accommodate users having knock-knees or related conditions.

19. A device as recited in claim 9 wherein said clamp means each comprise a U-shaped clamp having leg portions that are open at one end, and receive said circular cross-section rod portions at an opposite end; and wherein release of said clamp means is provided by a threaded fastener which passes through said legs adjacent said open end thereof, said threaded fastener also threadedly engaging either said foot plate or said leg support means.

20. A device as recited in claim 9 wherein said leg support means comprises a rigid angle member having a first portion operatively connected to said first clamp means, and having a second portion remote from said first clamp means; each of said first and second portions of said right angle member having strap means associated therewith for attaching said first and second portions to the leg of a user.

* * * * *